United States Patent [19]

Loh et al.

[11] Patent Number: 5,101,063

[45] Date of Patent: Mar. 31, 1992

[54] PREPARATION OF URETHANES BY CARBONYLATION

[75] Inventors: Kuo-Liang Loh, Taipei, Taiwan; Puh Shieh, El Toro, Calif.; Jih-Liang Chen; Tsu-Kung Chuang, both of Taiwan, Taiwan

[73] Assignee: Industrial Technology Research Institute, Hsinchu, Taiwan

[21] Appl. No.: 503,779

[22] Filed: Apr. 3, 1990

[51] Int. Cl.$^5$ .................. C07C 269/00; C07C 271/00
[52] U.S. Cl. ...................................... 560/24; 560/134; 560/157; 560/162; 560/163
[58] Field of Search .................. 560/24, 157, 162, 163, 560/134

[56] References Cited

U.S. PATENT DOCUMENTS 4,695,645  9/1987  Merger et al. .................. 560/24

FOREIGN PATENT DOCUMENTS 0083096  7/1983  European Pat. Off. .............. 560/24

Primary Examiner—Jose G. Dees
Assistant Examiner—Porfirio Nazario
Attorney, Agent, or Firm—Cushman, Darby & Cushman

[57] ABSTRACT

A process for preparation of urethanes by reacting an organic hydroxyl group-containing compound and carbon monoxide with a primary amine and oxygen in the presence of a non-noble metal or lanthanide metal catalyst system, particularly a cerium catalyst.

11 Claims, No Drawings

PREPARATION OF URETHANES BY CARBONYLATION

FIELD AND BACKGROUND OF THE INVENTION

Urethane can be catalytically or thermally decomposed to form corresponding isocyanates which are important key materials in the polyurethane (PU) industry as well as in the pharmaceutical industry. Hence, use of toxic phosgene can be avoided in the preparation of isocyanates from urethane. One efficient way to prepare urethane is oxidative alkoxycarbonylation of primary amine, which can be represented by the following general reaction equation:

$$R(NH_2)_x + xCO + xR'OH + x/2 O_2 \longrightarrow R(NHCOOR')_x + xH_2O \quad (I)$$

In this formula, R is the organic radical of the corresponding primary amino group-containing compound, R' is the organic radical of the hydroxyl group-containing compound, and x is an integer.

In the prior art, the disclosed catalyst system for this process is mainly group VIIIB metals of the periodic table, in combination with nitrogen-or phosphorous-containing compounds or halides as promoters.

U.S. Pat. No. 4,297,501 discloses a catalyst system comprising halides of a noble metal of the VIIIB group of the periodic table, and a compound capable of undergoing redox reactions. Also, European Pat. Appl. 083,095 discloses a process for preparing urethane in the presence of a catalyst system comprising the Pt group metals and halides of alkali metals or alkaline earth metals.

The fact that the disclosed patents use expensive noble metal catalysts partially diminishes the commercial interest in the known processes.

SUMMARY OF INVENTION

The instant invention relates to a process for preparing urethanes by the method of reacting an organic hydroxyl group-containing compound and carbon monoxide with a primary amine and oxygen in the presence of a non-noble metal catalyst system. The reaction is in accordance with the known oxidative alkoxycarbonylation reaction as shown in equation (I) above.

In the process according to the instant invention, one embodiment utilizes the lanthanide metals (elements of atomic numbers 57 through 71) as catalysts for the reaction. Another embodiment utilizes a cerium catalyst system for the reaction, preferably a mixture of a cerium catalyst with alkali salt or quaternary ammonium salt as promoter. High selectivity for urethane can be achieved at high conversion of the starting primary amine.

In essence, this invention has the advantage that a relatively inexpensive, yet highly active, cerium based catalyst system is employed. High yields of urethanes, e.g. desirably on the order of 90% and above conversion rate and 90% and above urethane selectivity, can be obtained without requiring phosgene.

DETAILED DESCRIPTION OF THE INVENTION

Suitable primary amines employed in the invention include organic compounds containing at least one primary amino group, as represented by the following general formula:

$$R(NH_2)_x$$

Where R and X are the same as defined above.

Exemplary primary amines of the above type include aliphatic amines such as methylamine, hexylamine, and the like, and aromatic amines such as aniline, 2,6-diaminotoluene, and the like.

Suitable organic hydroxyl group-containing compound, or alcohols which may be used include those which contain at least one aliphatic alcoholically bound hydroxyl group, or at least one phenolically bound hydroxyl group, as represented by the following general formula:

$$R'(OH)_x$$

wherein R' is the same as defined above, i.e. an aliphatic group containing 1 to 20 carbon atoms, such as alkyl and cycloalkyl, which may be substituted with one or more aromatic groups such as alkyl and cycloalkyl groups, or an aromatic group containing 6 to 20 carbon atoms, e.g. containing 6 to 10 ring carbon atoms, such as phenyl, naphthyl, and the like which may be substituted with one or more aliphatic groups such as alkyl groups, and x is the same as defined above.

Exemplary alcohols of above type include aliphatic alcohols such as methanol, ethanol, n-propanol, isopropanol, pentanol, benzyl alcohol, ethylene glycol, glycerol, hexanetriol, and the like, and aromatic alcohols such as phenols neththols, and the like.

Aliphatic alcohols, as distinguished from aromatic alcohols, such as phenols and naphthols, are the preferred hydroxyl group-containing compounds.

The non-noble metal catalyst system used in the process of the instant invention include a mixture of a non-noble metal catalyst with alkali metal salts or quaternary ammonium salts as promoter.

Suitable non-noble metal catalysts include pure oxides of non-noble metals as well as a non-noble metal supported on appropriate carriers such as active carbon, alumina, silica, zeolite or organic resins.

The lanthanide metal catalyst system used in the process of the instant invention includes a mixture of a lanthanide metal catalyst with alkali metal salts or quaternary ammonium salts as promoter.

Suitable lanthanide metal catalysts include pure oxides of lanthanide metals as well as a lanthanide metal supported on appropriate carriers such as active carbon, alumina, silica, zeolite or organic resins.

Of the non-noble metal and lanthanide metal catalyst systems, the non-noble cerium catalyst system is presently preferred. The non-noble cerium catalyst system used in the process of the instant invention include a mixture of a cerium catalyst with alkali metal salts or quaternary ammonium salts as promoter.

Suitable cerium catalysts include pure ceric oxide a well as cerium supported on appropriate carriers such as active carbon, alumina, silica, zeolite or organic resins; the $CeO_2$ and Ce supported on active carbon being preferred.

Suitable alkali metal salts which may be used as promoter include alkali metal salts, in particular alkali metal halides, such as lithium iodide, sodium iodide, potassium iodide, cesium iodide, lithium bromide, sodium bromide, rubidium bromide, potassium bromide, cesium bromide, and the like.

Suitable quaternary ammonium salts which may be used as promoter include aliphatic quaternary ammonium halides, e.g. tetraalkylammonium halides, and in particular iodides and bromides, such as tetraethylammonium iodide and tetraethyl-ammonium bromide and the like.

The process of the instant invention can be carried out in the absence of a solvent. However, an inert organic solvent can be used if necessary or desired, such as benzene, chlorobenzene, xylene, and the like.

The amount of the cerium catalyst employed in the reaction as catalyst is generally equivalent to about 0.001 to 0.4 moles cerium element per mole of the primary amine used. Cerium catalyst is generally in the form of ceric oxide or supported on appropriate carrier such as active carbon, alumina and the like. The amount of the alkali salts as promoter employed is generally equivalent to about 0.001 to 0.8 moles per mole of the primary amine used.

Exemplary preferred ranges are about 0.005 to 0.2 moles cerium catalyst, and about b 0.01 to 0.4 moles promoter, per mole of primary amine used.

Desirably, the molar ratio of promoter to cerium is about 1-5:1.

A molar excess of the organic hydroxyl group-containing compound, such as an aliphatic alcohol, is normally used e.g. about 5-30, especially about 10-25 moles of alcohol per mole of primary amine.

The amount of carbon monoxide used in the process of the instant invention is generally about 2 to 500, preferably about 10-200 moles per mole of primary amine used.

The amount of oxygen is about 0.5 to 5 moles of oxygen per mole of primary amine used.

The reaction is generally carried out at a pressure of about 200 to 8000 psig, preferably at about 400-2000 psig, and at a temperature of about 100 to 300° C., preferably at about 125°-200° C. The reaction time is usually about ½ to 4 hrs, depending on the reaction pressure and temperature selected.

The mixture of hydroxyl group-containing compound, primary amine, cerium catalyst and associated promoter is charged into an autoclave, optionally with an inert solvent. The autoclave is then pressurized with carbon monoxide and oxygen at room temperature, followed by heating with mixing agitation for the desired reaction time, after which the autoclave is cooled, and the reaction mixture is filtered and analyzed by GLC.

The major intermediate product observed in N, N'-diphenylurea.

The following examples are merely illustrative of preferred embodiments of the invention. Many variations thereon may be made without departing from the spirit of the disclosed invention, as will be evident to those skilled in the art, and such variations are intended to come within the scope of what is claimed.

EXAMPLE 1-3

A mixture containing 0.47 g (5 mmole) aniline, 0.017 g $CeO_2$ (0.1 mmole Ce element), 6.0 ml (100 mmol) ethanol and 0.2 mmole of the promoter if desired as listed in Table 1, were introduced into a 125 ml autoclave. The autoclave was then pressurized with 960 psig carbon monoxide and 40 psig oxygen at room temperature. The mixture was then heated to 180° C. and stirred for 2 hrs. After cooled to room temperature, the autoclave was vented and flushed with nitrogen, the mixture was discharged, filtered and analyzed by G.C.

The results are shown in Table 1. The selectivity indicated being based on aniline.

TABLE 1

| Example No. | promoters | conversion, % Aniline | selectivity, % Urethane |
|---|---|---|---|
| 1 | — | 29.5 | 70.8 |
| 2 | CsI | 98.8 | 97.0 |
| 3 | Et₄NBr | 84.0 | 62.9 |

EXAMPLE 4

The procedure was the same as that per example 1, except a mixture of 2.33 g (25 mmole) aniline, 50 ml ethanol 0.5 mmole $CeO_2$ and. 1.0 mmol CsI were introduced into a 300 ml autoclave and sample was withdrawn for G.C. analysis at different time intervals as the reaction in progress.

The results are shown in Table 2.

TABLE 2

| Time (min) | conversion, % Aniline | selectivity, % Urethane |
|---|---|---|
| 10 | 29.3 | 37.0 |
| 30 | 56.4 | 77.5 |
| 60 | 78.9 | 93.7 |
| 90 | 90.4 | 93.8 |
| 120 | 94.8 | 93.4 |

EXAMPLE 5

The procedure was the same as that in example 4 except 760 psig carbon monoxide and 40 psig oxygen at room temperature was used.

The results ar shown in Table 3.

TABLE 3

| Time (min) | conversion, % Aniline | selectivity, % Urethane |
|---|---|---|
| 1 | 28 | 48 |
| 2 | 36 | 70 |
| 3 | 55 | 88 |
| 6 | 85 | 94 |
| 8 | 90 | 96 |

EXAMPLE 6-8

The procedure was the same as that in example 1-3, except that 0.14 g 10% Ce/C was employed as catalyst coupling with a series of alkaline iodides as promoter. The results are shown in Table 4.

TABLE 4

| Example No. | promoters | conversion, % Aniline | selectivity, % Urethane |
|---|---|---|---|
| 6 | LiI | 91 | 99 |
| 7 | NaI | 99 | 98 |
| 8 | KI | 92 | 84 |

EXAMPLE 9-10

The procedure was the same as that in example 7 except that 100 mmole of various other alcohols were used. The results are shown in Table 5.

TABLE 5

| Example No. | alcohols | conversion, % Aniline | selectivity, % Urethane |
|---|---|---|---|
| 9 | n-Butanol | 90 | 50 |
| 10 | Benzyl alcohol | 90 | 65 |

EXAMPLE 11

The procedure was the same as that in example 7, except that 0.07 g(20% Ce / Al$_2$O$_3$) (0.1 mmole of Ce element) was used as catalyst. The conversion of analine was 97% with 91% selectivity to urethane.

EXAMPLE 12

The procedure was the same as that in example 7 except that 5 mmole n-butyl amine was employed to replace aniline. The conversion of n-butylamine was 100% with 61% selectivity to urethane.

We claim:

1. A process for producing urethanes, comprising the steps of reacting an aliphatic alcohol, carbon monoxide, a primary amine and oxygen in the presence of a non-noble metal catalyst system at a temperature in a range of from 100° to 300° C. and at a pressure in a range of from 200 to 8000 psig.

2. Process of claim 1, wherein the aliphatic alcohol contains at least 1-20 carbon atoms.

3. Process of claim 1, wherein the non-noble metal catalyst system comprises a cerium catalyst.

4. The process of claim 1, wherein a promoter comprising alkali metal salts or quaternary ammonium salts is used.

5. Process of claim 1, wherein about 0.001 to 0.4 mole cerium catalyst is used per mole of the primary amine.

6. Process of claim 1, wherein about 0.01 to 0.8 mole promoter is used per mole of the primary amine.

7. Process of claim 1, wherein about 5-30 mole alcohol are used per mole of the primary amine.

8. Process of claim 1, wherein about 2-5000 moles carbon monoxide are used per mole of the primary amine.

9. Process of claim 1, wherein about 0.5-5 mole oxygen are used per mole of the primary amine.

10. Process of claim 1, wherein the reaction is carried out in the presence of an inert organic solvent.

11. The process of claim 3, wherein a promoter comprising alkali metal salts or quaternary ammonium salts is used.

* * * * *